United States Patent [19]

Masaki et al.

[11] Patent Number: 4,742,030

[45] Date of Patent: May 3, 1988

[54] SINTERED ZIRCONIA MATERIAL AND METHOD FOR MANUFACTURING THE MATERIAL

[75] Inventors: Takaki Masaki; Kiyokazu Shinjo, both of Otsu, Japan

[73] Assignee: Toray Industries, Inc., Tokyo, Japan

[21] Appl. No.: 900,581

[22] Filed: Aug. 26, 1986

[30] Foreign Application Priority Data

Sep. 6, 1985 [JP] Japan .............................. 60-196076
Apr. 24, 1986 [JP] Japan .............................. 61-95077

[51] Int. Cl.$^4$ .................... C04B 35/48; C01G 25/02
[52] U.S. Cl. .................................. 501/105; 501/103; 501/102; 423/608
[58] Field of Search ........................... 501/103, 105

[56] References Cited

U.S. PATENT DOCUMENTS

| | | | |
|---|---|---|---|
| 3,525,597 | 8/1970 | Mazdiyasni | 423/608 |
| 4,506,023 | 3/1985 | Guigonis | 501/105 X |
| 4,525,464 | 6/1985 | Claussen et al. | 501/105 X |
| 4,587,225 | 5/1986 | Tsukuma et al. | 501/105 |

FOREIGN PATENT DOCUMENTS

| | | | |
|---|---|---|---|
| 0032066 | 2/1983 | Japan | 501/105 |
| 0129188 | 12/1984 | Japan | 501/105 |
| 0200859 | 10/1985 | Japan | 501/105 |
| 0226496 | 11/1985 | Japan | 501/103 |
| 61-026562 | 2/1986 | Japan | 501/105 |

OTHER PUBLICATIONS

Tsukama, K. et al., "Hot Isostatic Pressing of Y$_2$O$_3$--Partially Stabilized Zirconia," *Am. Ceram. Soc. Bull.*, 64[2] 310-13 (1985).

*Primary Examiner*—William R. Dixon, Jr.
*Assistant Examiner*—James M. Hunter, Jr.
*Attorney, Agent, or Firm*—Birch, Stewart, Kolasch & Birch

[57] ABSTRACT

A sintered zirconia material containing at least 50 mol % tetragonal zirconia and 1.5-5 mol % yttria, from which carbon is substantially absent, the porosity of which is not greater than 0.6%, the pore size of which is not greater than 0.1 μm and the pores of which exist mainly at triple points of zirconia grain boundaries. The sintered zirconia material can be obtained by sintering the raw material zirconia powder, the green body or the presintered material containing tetragonal zirconia and yttria in a required amount and in an oxidizing atmosphere, by hot isostatic pressing.

The sintered material thus obtained has a high strength and high toughness, and particularly excellent properties for use under conditions of higher than 600° C. and can be used as a material of various industrial machines or tools.

41 Claims, 8 Drawing Sheets

FIG. IB
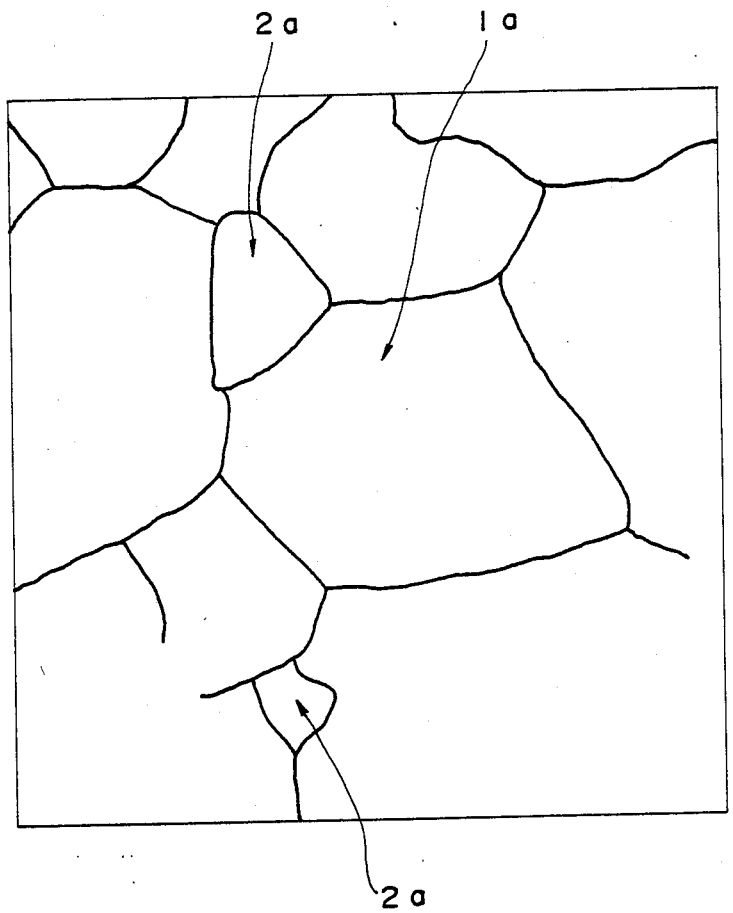

1c

F I G. 4 B
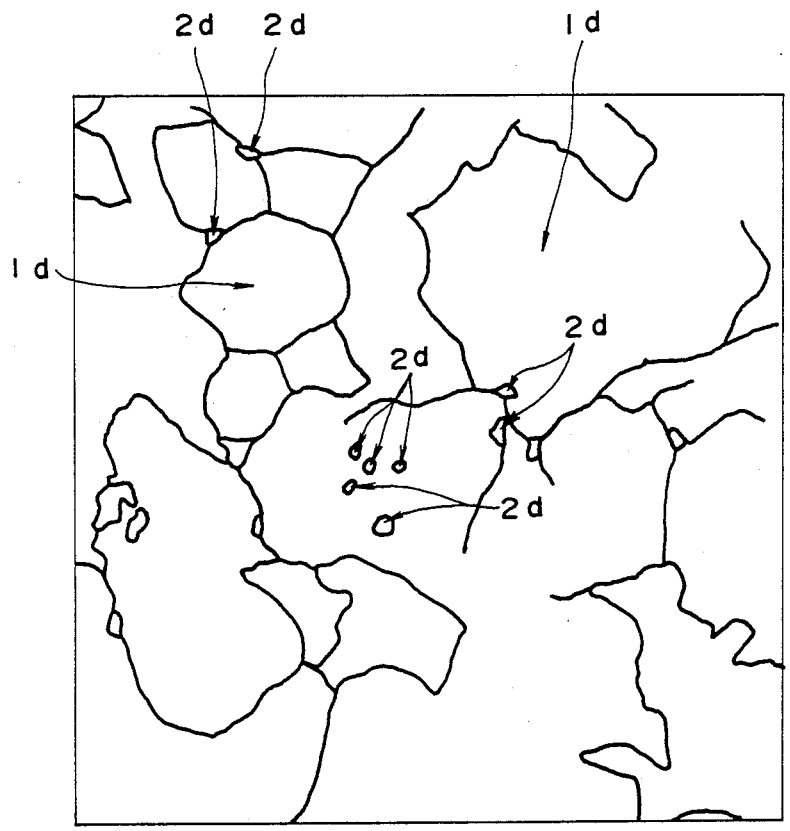

SINTERED ZIRCONIA MATERIAL AND METHOD FOR MANUFACTURING THE MATERIAL

BACKGROUND OF THE INVENTION

1. Field of the Invention

The present invention relates to a sintered zirconia material and a method for manufacturing the material.

2. Description of the Prior Art

There are several kinds of sintered zirconia materials. JP-A-57-111278 discloses, so called, a high strength sintered zirconia material. This conventional sintered zirconia material is a material containing 5-70 mol% zirconia having a tetragonal crystal structure (tetragonal zirconia) and the porosity of the material is 2-10%. In the sintered material, since the tetragonal zirconia is transformed to a zirconia having a monoclinic crystal structure (monoclinic zirconia) when receiving thermal shock and thereby expanding by about 4 vol. %, compressive stress fields are formed in the monoclinic zirconia or near the monoclinic zirconia. Since the compressive stress field acts so as to absorb strain due to the thermal shock, the strength against thermal shock of the sintered material is high. Also, since the compressive stress field acts so as to decrease an elastic strain energy when the material receives external stress, the bend strength of the material increases.

However, the increase in the bend strength is not so remarkable because the porosity is relatively high that is, 2-10%, and the deviation of the strength is large. Moreover, there is the defect that the toughness of the material is low.

On the other hand, JP-A-59-227770 discloses a sintered zirconia material obtained by sintering a zirconia powder containing a stabilizer and a black colorant in an inert atmosphere by hot pressing or hot isostatic pressing, using a graphite mold or die. It is described in the specification that the sintered material as obtained above has high heat resistance and high fracture toughness.

However, since the graphite mold is used and the material is sintered in an inert atmosphere, carbon remains in the material. Since the carbon evaporates by becoming carbon dioxide gas and a cavity is formed in the position where the carbon was positioned, when the material is used under temperature conditions of higher than 600° C., the strength of the material decreases greatly. Also, the strength of the material decreases even at room temperature.

SUMMARY OF THE INVENTION

An object of the present invention is to provide a sintered zirconia material having excellent mechanical properties, particularly high strength and high fracture toughness, and in which not only the deviation of the mechanical properties is very small, but also the strength thereof does not decrease, even if the material is used under temperature conditions of higher than 600° C.

Another object of the present invention is to provide a method for manufacturing a sintered zirconia material, easily and securely which has the excellent properties as described hereinabove.

To accomplish the above objects, a sintered zirconia material, according to the present invention, is provided which comprises:

(a) a sintered material containing at least 50 mol% zirconia having a tetragonal crystal structure;
(b) a sintered material containing 1.5-5 mol% yttria;
(c) a sintered material from which carbon is substantially absent;
(d) a porosity of the sintered material being not greater than 0.6%;
(e) a pore size of the sintered material being substantially not greater than 0.1 μm; and
(f) pores of the sintered material existing mainly at triple points of the zirconia grain boundaries.

A method for manufacturing a sintered zirconia material according to the present invention comprises the steps:

(a) preparing a zirconia powder containing 1.5-5 mol% yttria powder;
(b) making a raw material zirconia powder formed as a solid solution with yttria by milling the powder after calcining the powder at 800°-1000° C.;
(c) forming a green body by compacting the raw material zirconia powder;
(d) making a presintered material having a bulk density which is not less than 95% of the theoretical density by presintering the green body; and
(e) sintering the presintered material in an oxidizing atmosphere by hot isostatic pressing.

In the present invention, other methods are also applied as follows:

A method for manufacturing a sintered zirconia material comprises the steps:

(a) preparing a zirconia powder containing 1.5-5 mol% yttria powder;
(b) making a raw material zirconia powder formed as a solid solution with yttria by milling the powder after calcining the powder at 800°-1000° C.;
(c) forming a green body by compacting the raw material zirconia powder; and
(d) putting the green body into a capsule, and presintering and sintering the green body in an oxidizing atmosphere by hot isostatic pressing.

Another method for manufacturing a sintered zirconia material comprises the steps:

(a) preparing a zirconia powder containing 1.5-5 mol% yttria powder;
(b) making a raw material zirconia powder formed as a solid solution with yttria by milling the powder after calcining the powder at 800°-1000° C.; and
(c) filling the raw material zirconia powder in a capsule, and presintering and sintering the raw material zirconia powder by directly consolidating it in an oxidizing atmosphere using hot isostatic pressing.

The sintered zirconia material and the methods for manufacturing the material according to the present invention will now be described hereunder in detail.

In the present invention, first, a zirconia powder containing an yttria powder is prepared as follows. After an aqueous solution containing zirconium chloride having a purity of not less than 99.9% and an aqueous solution containing yttrium chloride having a purity of not less than 99.5% are mixed in a predetermined ratio, a zirconia powder which has an average grain size of not greater than 0.1 μm and which contains 1.5-5 mol% yttria is prepared, using a conventional coprecipitation method, a hydrolysis method, a thermal decomposition method, a metal alkoxide method, a sol-gel method or a vapor phase method etc. A powder can also be prepared from an aqueous solution containing zirconium nitrate having a purity of not less than 99.9% and an aqueous solution containing yttrium nitrate having a purity of not less than 99.5%, or from a pure zirconia powder having a purity of not less than 99.9% and a yttria powder having a purity of not less than 99.9%.

Next, the powder is milled in a ball mill, after it is calcined at 800°–1000° C., preferably at 850°–950° C. In accordance with requirements, the above calcination and milling can be repeated. Thus a raw material powder is obtained. The raw material powder obtained forms a solid solution in which the pure zirconia powder and the yttria powder are uniformly mixed. Although the zirconia in the solid solution reveals a different phase in accordance with the purity, grain size, mixing ratio and temperature and time of the calcination of the zirconia, usually it forms a mixing phase of a monoclinic symmetry and a tetragonal symmetry.

Next, the raw material powder is compacted to a green body having a required shape, using a conventional forming method such as rubber pressing, injection, die pressing or slip casting etc.

Next, the green body is set in a furnace. First, the green body is heated to 850°–1,000° C., preferably to 900°–950° C., at a heating rate of 20°–100° C./h, preferably of 30°–70° C./h. Subsequently, it is heated to 1150°–1550° C., preferably to 1200°–1450° C., more preferably to 1300°–1400° C., at a heating rate of 30°–50° C./h, and is maintained at that temperature for several hours after the second heating. By these heating steps and subsequent maintenance heating, a presintered material having a bulk density which is not less than 95% (desirably not less than 97.5%, and more desirably not less than 99%) of the theoretical density is obtained. In the stage of the above heating, the crystal structure of zirconia is transformed from the mixing phase of a monoclinic symmetry and tetragonal symmetry to a tetragonal symmetry, a mixing phase of tetragonal symmetry and cubic symmetry or a cubic symmetry. The temperature causing such a transformation and the rate of transformation depends on the amount of yttria. Therefore, the temperature for the presintering is determined within the above range, considering the phase diagram of used zirconia so that the above crystal structure can be obtained. When the material is cooled after presintering, the crystal structure of zirconia changes although the degree of the change depends on the cooling rate. In the zirconia having a tetragonal crystal structure, a part of the tetragonal zirconia changes to monoclinic zirconia; in the zirconia having the mixing phase of a tetragonal symmetry and a cubic symmetry, a part of the tetragonal zirconia changes to monoclinic zirconia and a part of the cubic zirconia changes to tetragonal zirconia, and a part of the tetragonal zirconia further changes to monoclinic zirconia. In the zirconia having a cubic crystal structure, a part of or most of the cubic zirconia changes to tetragonal zirconia, moreover a part of the tetragonal zirconia changes to monoclinic zirconia. Eventually, a mixing phase of tetragonal, monoclinic and cubic symmetry is generated.

Next, the presintered material is sintered. In the sintering according to the present invention, the material is sintered in a controlled oxidizing atmosphere by hot isostatic pressing (hereinafter, also called "HIP"). The presintered material is heated and is maintained at 1150°–1500° C. (preferably at 1300°–1400° C.) for several hours under a pressure of 1000–2200 kg/cm$^2$ (preferably 1500–2000 kg/cm$^2$). After that, the material is cooled at a cooling rate of 200°–600° C./h (preferably of 300°–500° C./h). Thus a sintered zirconia material is obtained.

The oxygen concentration of the oxidizing atmosphere in the HIP is controlled to 0.1–25 vol.%, preferably to 1–20 vol.%, more preferably to 3–10 vol.%. If the concentration is less than 0.1 vol.%, the oxygen concentration is too low, and the material is deoxidized by the gas released from the members constituting the furnace etc., whereby carbon remains in the sintered material. If the concentration is greater than 25 vol.%, the oxygen concentration is too high so that the fire point of the members constituting the furnace largely decreases and such a condition greatly decreases the life span of the furnace. Accordingly it is not practical.

Generally there are two typical methods in the treatment due to HIP. One is containerized powder consolidation by HIP and the other is containerless HIP of presentered materials. In the former method, the raw material powder is filled or the green body is put in a glass, ceramic or metal container (called "capsule"), sealed and then directly sintered. In the latter method, after the presintered material having a bulk density which is not less than 95% of a theoretical density is made as described hereinabove, it is sintered by HIP without a capsule.

The former method has an advantage that a fine sintered material can be obtained even if the temperature of the treatment is relatively low. However, since a container must be used, it is difficult to apply the method to manufacturing of a sintered material having a complicated shape. The latter method does not have such a restriction. However, since the material is pressed by gas, pores of the presintered material must not be open pores but closed pores. In this matter, almost all of the pores of the presintered material having a bulk density of not less than 95% of a theoretical density are closed pores, and there is no problem in the pressing. In such a HIP, the presintered material is firmly consolidated, the strength of bonding between crystal grains increases and a sintered compact having excellent mechanical properties is obtained. Moreover, a fine sintered material is obtained even under the condition of relatively low temperature. In the former method, a presintered material having a low bulk density also can be used instead of the green body. Since the water absorptivity of such a presintered material is low and the contraction of the material is accelerated compared with the raw material powder or the green body, even if the bulk density is relatively low, it can be easy to manufacture a sintered material having a complicated shape by using the presintered material instead of the raw material powder or the green body.

HIP must be carried out in an oxidizing atmosphere as aforementioned. Generally HIP is carried out in an inert atmosphere such as an argon gas atmosphere using a heater constructed from carbon, etc. However, if HIP is carried out in such a manner, a trace quantity of carbon or carbon monoxide remains in the sintered material. When the sintered material obtained by such a manner is used under the condition of higher than 600° C., the remaining carbon or carbon monoxide becomes carbon dioxide gas and it evaporates. As a result, a cavity is formed in the position where the carbon or carbon monoxide has been positioned, thereby greatly decreasing the high temperature strength of the sintered material.

The crystal structure of zirconia before sintering is a tetragonal symmetry, a mixed phase of a tetragonal symmetry and a cubic symmetry or a cubic symmetry. The crystal structure changes when it is cooled, depending on the cooling rate. In the case of zirconia having a tetragonal crystal structure, a part of the tetragonal crystal structure changes to a monoclinic crystal structure. In the zirconia having a tetragonal and cubic crystal structure, a part of the tetragonal crystal structure changes to monoclinic, a part of or most of the cubic crystal structure changes to tetragonal and a part of the changed tetragonal crystal structure further changes to a monoclinic structure. Eventually the crystal structure changes to a mixing phase of a tetragonal, monoclinic and cubic symmetry. In the case of zirconia having a cubic crystal structure, a part of or most of the cubic crystal structure changes to tetragonal and a part of the changed tetragonal crystal structure further changes to the monoclinic structure.

The amount of tetragonal zirconia in the sintered compact depends on various conditions such as the purity, grain size and composition of the raw material powder, the density of the presintered material, the temperature and time of sintering and the cooling condition after sintering. Accordingly, these conditions must be strictly controlled. In the present invention, the amount of tetragonal zirconia must not be less than 50 mol%. Preferable the amount of tetragonal zirconia is not less than 70 mol%, and more preferable the amount is not less than 80 mol%.

A zirconia containing tetragonal zirconia is strengthened and increased in toughness by a transformation of the crystal structure from the tetragonal to the monoclinic system when the zirconia receives an external stress. This mechanism is called "stress induced transformation mechanism". To sufficiently reveal the effect of increasing the strength and toughness due to the stress induced transformation mechanism, the amount of tetragonal zirconia must not be less than 50 mol%.

In the above, the amount of tetragonal zirconia($C_T$) (mol%) is determined and defined as follows.

The sintered zirconia material is sliced, ground by a stone of #150–300 and the ground sample is polished by a diamond paste. The polished surface of the sintered material is subjected to an X-ray diffraction method, whereby a diffraction intensity A (an area intensity, hereunder expressed similarly) of the 111 plane of tetragonal zirconia, a diffraction intensity B of the 111 plane of monoclinic zirconia and a diffraction intensity C of the 111 plane of monoclinic zirconia are recorded. $C_T$ is calculated from the following equation using the above data. Here, for the diffraction intensities, the data amended by the Lorentz factor are applied.

$$C_T = (A/(A+B+C)) \times 100$$

The 111 plane of tetragonal zirconia is diffracted almost together with the 111 plane of cubic zirconia. Accordingly, since it is difficult in an X-ray diffraction method to divide the diffraction intensities of both planes, the data obtained together is used as a value of the diffraction intensity of the 111 plane of tetragonal zirconia.

The Lorentz factor L is shown in the following equation.

$$L = (1 + \cos^2 2\theta)/(\sin^2 \theta \times \cos \theta)$$

The diffraction conditions are as follows.
(i) The X-ray generation device utilized is RU-200B produced by Rigakudenkisha (a Japanese company). This device is a rotary pair cathode type and for an X-ray source, CuK$_\alpha$-ray and a curved crystal type monochromator are used.
(ii) The goniometer is the 2155D type produced by Rigakudenkisha. The slit system in this meter is 1°–0.15 mm-1° and the detector is a scintillation counter.
(iii) The count recorder is the RAD-B type produced by Rigakudenkisha.
(iv) The scan system is a 2 $\theta/\theta$ scan and step scan.
(v) The range of measurement (2$\theta$) is 27°–33° and 70°–76°.
(vi) The step of the count (2$\theta$) is 0.01°.
(vii) The time of count is 1 second/step.

In the same manner as above, the amount of cubic zirconia $C_c$ (mol%) is determined and defined from the following equation.

$$C_c = (D/(D+E+F)) \times 100$$

Wherein, D is the diffraction intensity of the 400 plane of cubic zirconia, E is the diffraction intensity of the 004 plane of tetragonal zirconia, and F is the diffraction intensity of the 220 plane of tetragonal zirconia.

When the amounts of tetragonal zirconia and cubic zirconia are determined by the above equations, the remainder is monoclinic zirconia.

Monoclinic zirconia sometimes forms microcracks and a compressive stress field around it. If too many cracks are formed, the strength and toughness of the sintered material decreases. Therefore, the amount of monoclinic zirconia is desirably not greater than 10 mol% in view of the above facts. On the other hand, the tetragonal zirconia in the sintered zirconia material has a stress induced transformation mechanism, and it is felt that there must be nuclears in order to cause the transformation. From this view point, to possess a small amount of monoclinic zirconia is preferable. Namely, the existence of monoclinic zirconia causes microcracks or minute defects and they function as nuclears. Although the nuclears are necessary to cause the stress induced transformation, they decrease the strength of the sintered material if too many are present. Therefore, in the present invention, it is desirable to suppress the amount of monoclinic zirconia to not greater than 10 mol%, considering the balance between the promotion of the stress induced transformation and maintaining the strength.

Next, the reason why it is desirable to contain cubic zirconia can be explained as follows.

The cubic crystal structure is the highest with respect to thermostability among the three crystal structures. Therefore, by the presense of cubic zirconia, the heat resistance and the corrosion resistance of the sintered material on the high temperature use can be increased. The cubic zirconia present in the sintered material containing at least 50 mol% tetragonal zirconia exists in the state of dispersion around the tetragonal zirconia, forming a matrix and/or between the grains of the tetragonal zirconia. When moisture, acid or alkali acts on a sintered zirconia material, the stability of tetragonal zirconia decreases, a part of tetragonal zirconia transforms to monoclinic symmetry and microcracks are generated in the intergranular position of the tetragonal zirconia. The microcracks can become origins for the destruction of the sintered material. However, if cubic zirconia is present to a certain extent in the sintered material, the progress of the destruction is suppressed to a great extent because the cubic zirconia does not accompany the deformation such as described in the above, and whereby the heat resistance and the corrosion resistance of the material are increased. These increased properties are very desirable for a sintered material used at a high temperature or under other severe conditions.

In the present invention, the sintered zirconia material contains 1.5–5 mol% yttria as a stabilizer. This range of 1.5–5 mol% is a necessary condition to maintain the amount of tetragonal zirconia to not less than 50 mol%. However, this is not the only condition. Namely, the amount of tetragonal zirconia also depends on the raw material powder, the condition of presintering, the condition of sintering etc. as aforementioned. By the cooperation of these conditions and the amount of yttria, the amount of not less than 50 mol% of tetragonal zirconia can be achieved. If the amount of yttria is less than 1.5 mol%, a rapid transformation from tetragonal zirconia to monoclinic zirconia is caused in the cooling process, and many cracks due to the monoclinic zirconia are generated in the sintered material, thereby decreasing the strength and toughness of the material. If the amount of yttria is more than 5 mol%, it becomes difficult to control the amount of tetragonal zirconia to not less than 50 mol% with the condition of sintering or cooling, thereby also decreasing the strength and toughness of the material. The amount of yttria is preferably 1.75–4.5 mol%. To increase the toughness of the material, more preferable the amount is 1.75–2.25 mol%. To increase the strength of the material, the amount is preferably 2.5–3.2 mol%. To increase the heat resistance or high temperature strength under higher than 600° C. of the material, more preferable the amount is 3.5–4.5 mol%. By using yttria, sintering under the condition of a relatively low temperature can be possible and a fine sintered material can be obtained. However, other stabilizer can be used together. For example, an oxide which forms a solid solution together with zirconia, such as magnesia, calcia or ceria can be used together with yttria as a stabilizer.

In the sintered material according to the present invention, carbon which causes a decrease in the strength of the material at higher than 600° C. is substantially absent from the material as aforementioned. "Substantially absent" is defined as follows.

There are several methods for analyzing the amount of carbon in a sintered zirconia material, for example, an infrared absorptiometric method, SIMS (Secondary Ion Mass Spectrometry), and laser Raman spectral analysis. In the present invention, the laser Raman spectral analysis is applied. When the sintered material is excited by a ray with 4880 Å and 4579 Å wave length using argon laser, the case where the amount of carbon detected as amorphous carbon is almost absent from the material is defined "substantially absent". The conditions of the measurement are shown as follows.

Equipment is Ramanov U-1000 (produced by Jobin Yuon, a French Company),
wave lengths of laser are 4880 Å and 4579 Å,
voltage of the supply is 1650 V,
gate time is 1.0 second,
scan speed is 60 $cm^{-1}$/min,
scan inc is 0 $cm^{-1}$,
delay time is 0 second,
sample interval is 1 $cm^{-1}$,
repeat time is 3,
spectral range is from 1800 $cm^{-1}$ to 1100 $cm^{-1}$.

Next, in the present invention, the porosity of the sintered material must not be greater than 0.6% and the pore size must be substantially not greater than 0.1 $\mu$m. Here, the porosity P (%) is defined by the following equation.

$$P=(1-(\text{bulk density/theoretical density}))\times 100$$

A theoretical density $d_{th}$ is obtained by the following equation.

$$d_{th}=4M/(d^3N)$$

wherein,
N is Avogadro constant ($6.02\times 10^{23}$ $mol^{-1}$),
M is the molecular weight of zirconia, and
d is the lattice parameter.

The value of d depends on the crystal structure of zirconia and the amount of yttria and is determined by the X-ray diffraction method. In the present invention, the theoretical density of tetragonal zirconia is 6.03–6.09 g/cm$^3$, that of cubic zirconia is 5.98–6.04 g/cm$^3$ and that of monoclinic zirconia is 5.65–5.75 g/cm$^3$. The strength of the sintered material and the deviation of the strength are influenced by the porosity, and at the same time influenced by pore size. The pores cause stress concentration field. When the porosity becomes more than 0.6% or the pore size becomes more than 0.1 $\mu$m, the decrease of the strength and the deviation of the strength of the sintered material increases suddenly. Therefore, in the present invention, the porosity is restricted to be not greater than 0.6% and the pore size is restricted to be not greater than 0.1 $\mu$m, preferably to be not greater than 0.05 $\mu$m, so as to prevent the sintered material from having the above defect. Preferable the porosity of the sintered material is not greater than 0.4%, more preferable the porosity is not greater than 0.3%. In this technical field, Weibull modulus is used to indicate the statistical deviation of strength. The larger the Weibull modulus of the material becomes, the smaller the deviation of the strength of the material becomes and the higher the reliability of the material becomes. This Weibull modulus is defined as follows. When the distribution function shown by Weibull is applied to the strength distribution of a material, the following equation stands.

$$P_s(v)=\exp(-V(\sigma-\sigma u)/\sigma o)^m$$

wherein,
$P_s$ (v) is the applied stress of $\sigma$ and indicates the probability that a material having the volume of V does not break,
$\sigma$o is the normalization parameter,
$\sigma$u is the stress when the probability of breakage is 0,
m is Weibull modulus.

The Weibull modulus is regarded as a material constant indicating the deviation of the strength of a material. The larger the value of m becomes, the smaller the deviation of strength becomes.

Next, in the sintered material according to the present invention, pores of the material exist mainly at triple points of the zirconia grain boundaries. Here, the triple point is defined as follows. When a sliced sample (the thickness is not greater than 400–500 Å) is observed by a transmission electron microscope, a point where the crystal grains of not less than three grains are mutually connected is called "a triple point". The expression "exist mainly at the triple points" is defined as follows. First, the structure of the sintered material is observed by a transmission electron mocroscope at a magnification of 20,000-40,000; crystal grains of 50 are chosen from one scope adequately chosen, and the number of pores existing in the grains, the pores existing at the grain boundaries and the pores existing at the triple points are determined respectively from the 50 grains. Next, four other scopes are chosen and similarly the number of pores are determined from each 50 grains of the four scopes. As a result, the number of pores (N) and the number of the pores existing at triple points ($N_t$) are determined from five scopes. When $N_t/N$ is not less than 0.8, this state is defined as "exist mainly at the triple points". The ratio of $N_t/N$ is preferably not less than 0.9. Here, the scope having pores of not less than 5, locally concentrated within several grains, is not chosen for the determination. In accordance with requirements, the magnification of the microscope may be raised to 100,000-200,000 when counting the numnber of pores and the size of the pores.

In the measurement of the pore size, 250 grains are chosen similarly as described above. In the present invention, a pore size of the sintered material is substantially not greater than 0.1 μm. "Substantially not greater than 0.1 μm" is defined that not less than 80% of the pores existing at triple points ($N_t$) have a pore size of not greater than 0.1 μm. Desirably not less than 90% of the pores existing at the triple points have a pore size of not greater than 0.1 μm. Moreover, desirably the pore size is substantially not greater than 0.05 μm. In this case, "substantially not greater than 0.05 μm" is defined similarly as described above.

Generally, pores are originated in grains, at grain boundaries and at triple points. The pores in grains and the grain boundaries reveal when the sintered material is not sufficiently fine or the crystal grains have not grown sufficiently, and such pores greatly decrease the strength of the material. Although the pores existing at triple points also decrease the strength of the material, the degree of the decrease is not so high and these pores do not decrease the connecting strength between grains so much. Therefore, even if the pores exist at triple points, the strength of the sintered material is sufficiently maintained to exhibit the required strength.

The sintered material, according to the present invention has an average reflection coefficient of about 0.2-0.6 and a translucent function, and the color tone of the material is deep. The average reflection coefficient is determined as follows.

Using a spectroscope and choosing a white sintered alumina material as a standard sample, the spectral reflectance of the sintered material R and that of the standard sample Ro are determined in accordance with the wave length of 400-700 nm, and from them the spectral reflection factor $r_{80}$ at each wave length is obtained using the following equation.

$$R_\lambda = -\text{Log}(R/Ro)$$

An average reflection factor $r_m$ is obtained by integrating the spectral reflection factor asked by the above equation from 400 nm to 700 nm and dividing the obtained value with intervals of the wave length.

$$r_m = 1/300 \int_{400}^{700} r_\lambda d\lambda$$

wherein, a sphere having the diameter of 60 cm is used as an integrating sphere. In the measurement, the reflectance of the sintered alumina material is regarded as 100%. Moreover, the surface for the measurement of the standard sample is polished by a #400 emery paper.

In the sintered material according to the present invention, the material may contain a third component except yttria. If the sintered material additionally contains at least one metal oxide selected from the group consisting of aluminum, titanium, copper, nickel, iron, cobalt and chromium oxide in an amount of 0.1-1 wt.% as a third component, the strength and toughness of the material is further increased. More preferable amount of the third component is 0.2-0.5 wt.%.

When a coloured sintered material is required, the sintered material may contain a colorant in an amount of 0.01-2 wt.%. For example, when 0.05-0.7 wt.% chromium oxide or 0.05-0.2 wt.% copper oxide is added, the compact is tigned with a brown or green color. For pink color, 0.05-2 wt.% erbium oxide may be added. For a yellow color, 1-2 wt. % cerium oxide or 0.05-2 wt.% vanadium may be added. For a violet color, 0.5-2 wt.% neodymium oxide or 0.05-0.3 wt.% cobalt oxide may be added. For an orange color, 0.05-0.5 wt.% iron oxide may be added. A plurality of colorants may be used together.

BRIEF DESCRIPTION OF THE DRAWINGS

The objects, features and advantages of the present invention will become apparent and more readily appreciated from the following detailed description of the preferred exemplary embodiments of the invention, taken in conjunction with the accompanying drawings, in which:

FIG. 1B is a schematic view traced along the microphotograph shown in FIG. 1A;

FIG. 4B is a shematic view traced along the microphotograph shown in FIG. 4A.

DETAILED DESCRIPTION OF THE PREFERRED EMBODIMENTS

Figure 1A:
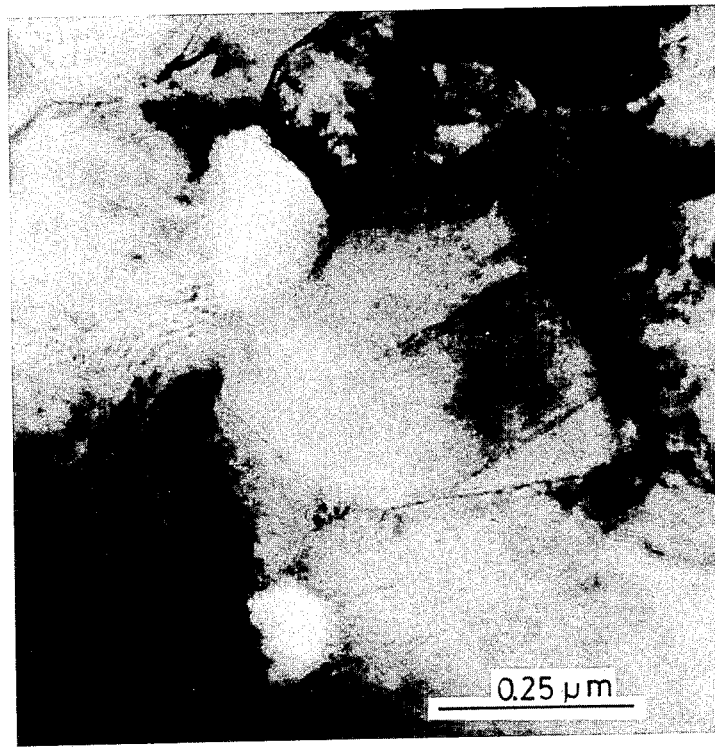
FIG. 1A is a microphotograph (magnification; 132,000) of a sintered zirconia material according to an embodiment of the present invention.

Some preferred embodiments of the present invention will be described hereunder refering to the attached drawings.

EXAMPLE 1

An aqueous solution containing zirconium chloride having a purity of 99.9% and an aqueous solution containing yttrium chloride having a purity of 99.9% are mixed so as to achieve 1.5 mol% yttria in a sintered material.

Next, the solution is gradually heated to about 100° C., is evaporated by maintaining it at that temperature for about 150 hours, and after that, is heated to about 900° C. at a heating rate of about 100° C./h, and by maintaining it at this temperature for about 3 hours, a calcined powder is obtained. Next, the calcined powder is milled with a ball mill lined with a polyurethane, and a raw material powder having an average grain size of about 0.07 μm is obtained.

Next, the raw material powder is formed into a green body, using a rubber pressing. The pressure for the pressing is about 4,000 kg/cm².

After that, the green body is placed in a furnace, where the body is heated first to about 900° C. at a heating rate of about 50° C./h. Next the body is heated to about 1,200° C. at a heating rate of about 40° C./h and after that the body is maintained at this temperature for about 2 hours, whereby a presintered material having a bulk density of about 98% of the theoretical density is obtained.

Next, the presintered material is sintered using HIP. The presintered material is heated by a platinum heater to about 1,200° C. at a heating rate of about 450° C./h in an oxidizing atmosphere in which about 3% oxygen is present and the remainder is argon gas. At the same time the gas pressure for pressing the material is raised to 2,000 kg/cm², and after maintaining this state for about 1.5 hours, the material is cooled at a cooling rate of about 400° C./h, thereby obtaining a sintered material.

With respect to the sintered material obtained as described above, the amount of tetragonal zirconia, the porosity, the pore size, the position of pores, the existence of carbon, the bend strength, the fracture toughness, the Weibull modulus, the bend strength after maintaining the material at 1,000° C. for 100 hours (hereinafter called a high temperature strength) were determined. For the measurement of the pore size and the position of the pores, the microstructure of the sintered material was observed by transmission electron microscopy (TEM, Hitachi Ltd. out put: 200 KW) on a thin film produced by cutting with a microtome and thinning by Ar ion bombardment. The bend strength ($\sigma_f$) was calculated from the following equation.

$$\delta f = \frac{3PL}{2bd^2}$$

where P is fracture load, L is the span length (=20 mm), b is the specimen width and d is the thickness.

For the measurement of the fracture toughness the IM method (indentation microfracture method) was applied.

This method relies on the formation of radial crack around the indentation of Vickers indenter load which exceeds the critical load ($P_c$) required for initiation of a crack. The test piece was polished to an optical finish. The lengths of Palmqvist cracks and indent developed in the specimen when it was subjected to Vickers indent load of 20 Kg were measured with a light microscope. The fracture toughness was then determined from the following equation developed by Niihara et al.

$$K_{1c}(\text{MPa }\sqrt{m}) = \frac{0.035}{\phi}\left(\frac{\phi E}{H}\right)^{0.4} \cdot H \cdot a^{0.5} \cdot \left(\frac{c-a}{a}\right)^{-0.5} \quad ((c-a)/a \leq 2.5)$$

wherein, $K_{1c}$ is the fracture toughness, E is the Young's modulus (~200 GPa), H is the Vickers hardness (MPa), $\phi$ is the constraint factor (~3), a is the half diagonal of the Vickers indent measured from the center of the indentation to the beginning of the surface crack, and c is the radius of the surface crack measured from the center of the indentation to the end of the crack.

The Weibull modulus was obtained after 20 measurements.

The resulting data were as follows.
amount of tetragonal zirconia: 88 mol%
porosity: 0.6%
pore size: 0.1 μm
position of pores: mainly at triple points
carbon: not detected
bend strength: 1,000 MPa
fracture toughness against breakage: 16 MPa $\sqrt{m}$
Weibull modulus: 14
high temperature strength: 980 MPa The microstructure of the sintered material was observed by transmission electron microscopy (TEM, Hitachi Ltd. out put: 200 KW) on a thin film produced by cutting with a microtome and thinning by Ar ion bombardment, as shown in FIG. 1A (magnification: 132,000). FIG. 1B is a schematic view traced along FIG. 1A. In FIG. 1B, the numeral $1_a$ shows a zirconia crystal grain and the numeral $2_a$ shows a pore. The pores $2_a$ exist at the triple points,

EXAMPLE 2

Figure 2A:
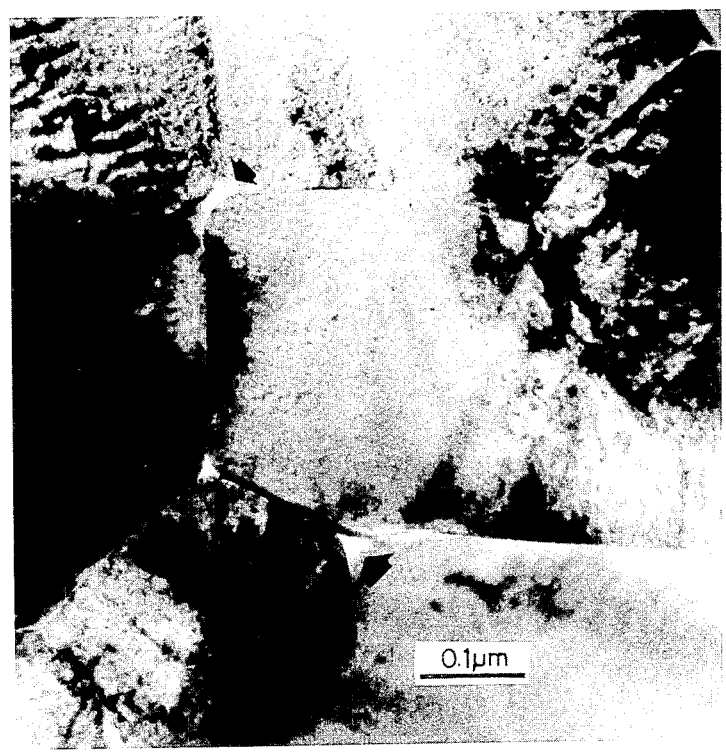
FIG. 2A is a microphotograph (magnification; 170,000) of a sintered zirconia material according to another embodiment of the present invention.
Figure 2B:
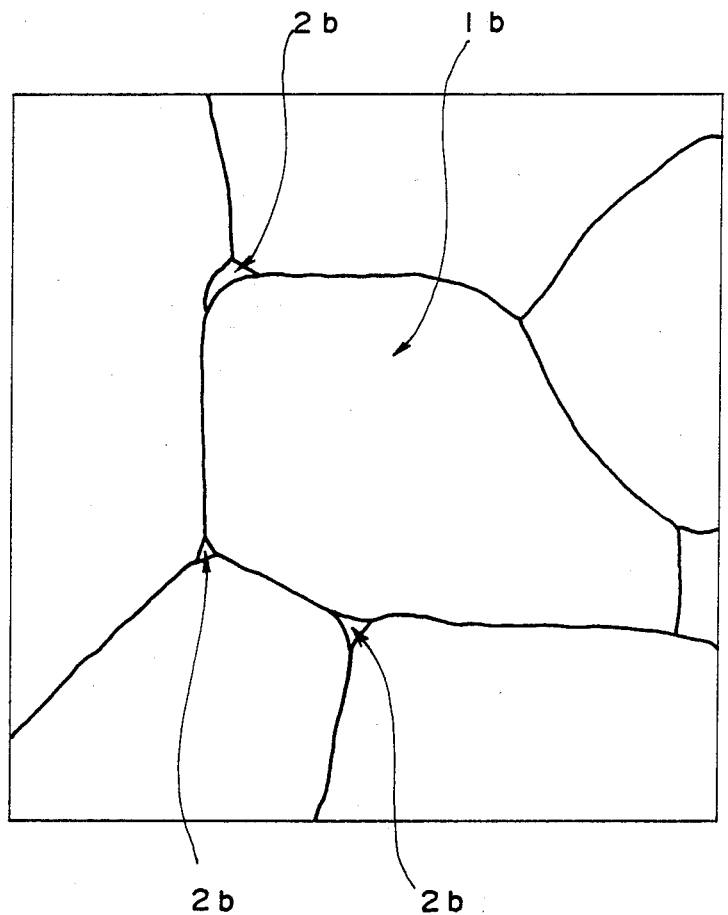
FIG. 2B is a schematic view traced along the microphotograph shown in FIG. 2A.

The amount of yttria was set so as to become 3 mol% in the sintered material. The temperature for presintering was 1,450° C. and the temperature for HIP was 1,400° C. Other conditions were the same as in example 1. The obtained material was determined in the same manner as in example 1. The resulting data were as follows.
amount of tetragonal zirconia: 92 mol%
porosity: 0.1%
pore size: 0.02 μm
position of pores: mainly at triple points
carbon: not detected
bend strength: 1,700 MPa
fracture toughness: 7.0 MPa $\sqrt{m}$
Weibull modulus: 15
high temperature strength: 1,650 MPa FIG. 2A (microphotograph, magnification: 170,000) shows the microstructure of the sintered material. FIG. 2B is a schematic view traced along FIG. 2A. In FIG. 2B, the numeral $1_b$ shows a zirconia crystal grain and the numeral $2_b$ shows pores. The pores $2_b$ exist at triple points.

EXAMPLE 3

Figure 3A:
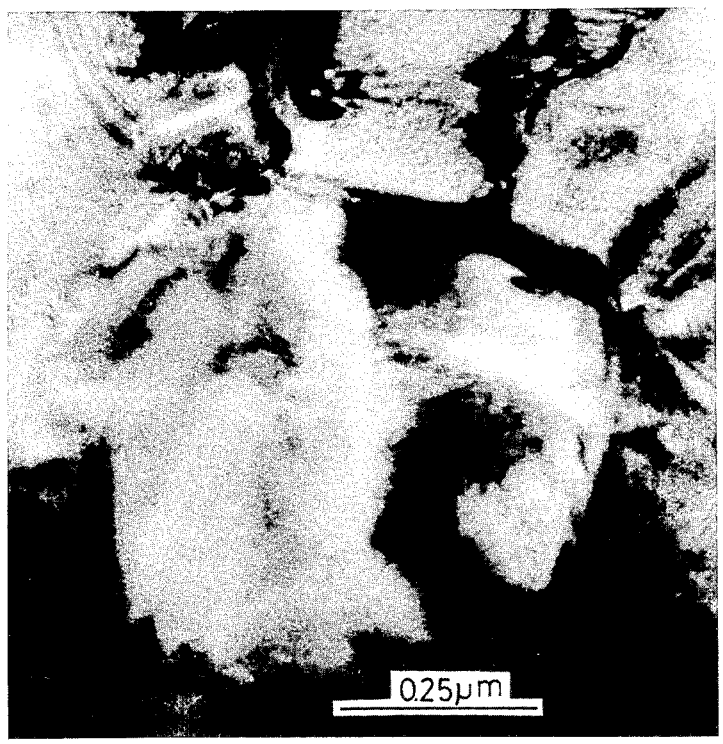
FIG. 3A is a microphotograph (magnification; 132,000) of a sintered zirconia material according to further embodiment of the present invention.
Figure 3B:
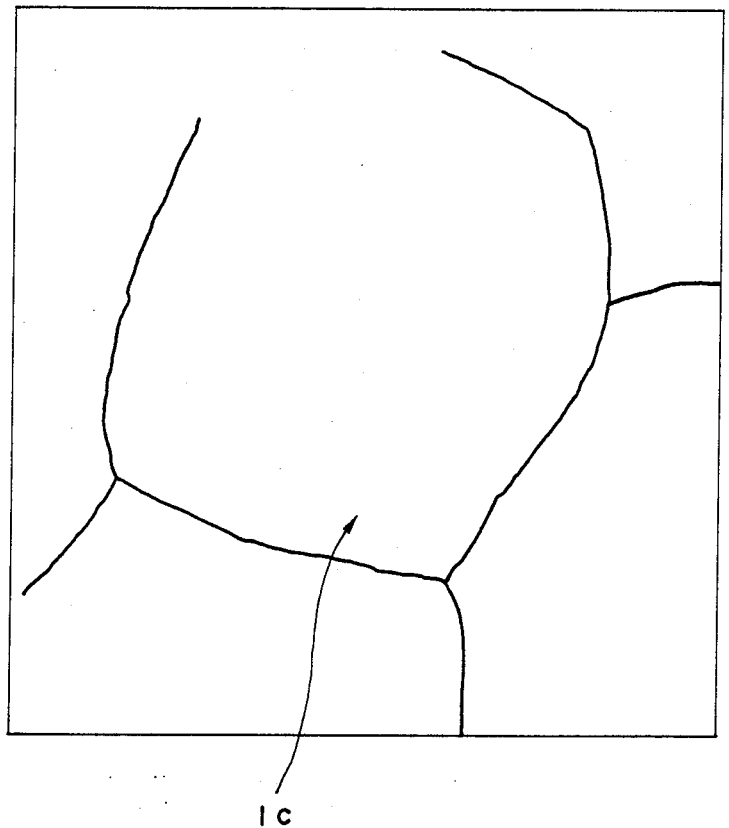
FIG. 3B is a schematic view traced along the microphotograph shown in FIG. 3A.

The amount of yttria was set so as to become 5 mol% in the sintered material. Other conditions were the same as in example 2. The resulting data were as follows:
amount of tetragonal zirconia: 55 mol%
porosity: 0.1%
pore size: not greater than 0.02 μm position of pores: mainly at triple points
carbon: not detected
bend strength: 1,350 MPa
fracture toughness: 5.2 MPa $\sqrt{m}$
Weibull modulus: 12
high temperature strength: 1,340 MPa FIG. 3A (microphotograph, magnification 132,000) shows the microstructure of the sintered material. FIG. 3B is a schematic view traced along FIG. 3A. In FIG. 3B, the numeral $1_c$ shows a zirconia crystal grain. Although pores are not revealed in this microphotograph, pores were determined in the other scopes observed by the microscope.

EXAMPLE 4

NiCl$_2$ having a purity of 99.5% was added to an aqueous solution so as to obtain 0.3 wt % NiO as a colorant in the sintered material. Other conditions were the same as in example 3. The sintered material obtained was determined in the same manner as in example 1, and at the same time the tristimulus values Y (lightness) and x,y (chromaticity coordinates) of the material were determined by CIE (Commission International de eEclairage) 1931 Standard Colorimetric System, using a colorimeter produced by Suga Shikenki K.K. (a Japanese company). This colorimeter comprises an illuminant, a lens system, a colored filter, a receiver having an optical system and a measuring part indicating and calculating data. The method of colorimetry is described along the reflection method aforementioned. First, the sintered material is out to a size of not less than 5 mm×5 mm (preferably not less than 20 mm×20 mm and the thickness is 3–5 mm). After the surface of the sample is polished by a #400 emery paper for measurement, the surface is polished by #600, #800, #1000 emery papers in order, and finally the surface is finished by lapping with a diamond paste having an average grain size of 3.0 μm. The sample obtained is located in a colorimeter, and the light from the illuminant is applied to the surface of the sample. The reflected light from the sample is integrated by an integrating sphere, and the light is received by the receiver through the colored filter set in the integrating sphere in accordance with the tristimulus values X, Y, Z. The electrical signals corresponding to the tristimulus values X, Y, Z from the receiver are measured by the measuring part and calculated to the predetermined color specification system (Y, x, y). Each colored filter of X (red), Y (green) and Z (blue) is based on CIE 1931 system and from the system the values of X, Y and Z can be obtained. Using X, Y, Z, the chromaticity coordinates (x, y) is obtained from the following equation.

$x = X/(X+Y+Z)$ $y = Y/(X+Y+Z)$ y shows lightness, white is 100(%) and black is 0(%).
The resulting data were as follows.
amount of tetragonal zirconia: 53 mol%
porosity: 0.1%
pore size: 0.02 μm
position of pores: mainly at triple points
carbon: not detected
bend strength: 1,300 MPa
fracture toughness: 5.0 MPa $\sqrt{m}$
Weibull modulus: 11
high temperature strength: 1,280 MPa
tristimulus values: Y=3.4, x=0.22, y=0.40 (color: Nile green)

EXAMPLE 5

CeCl$_3$ having a purity of 99.5% was added to an aqueous solution so as to obtain 1.0 wt % CeO$_2$ as a colorant in the sintered material. Other conditions were the same as in example 3. The resulting data determined in the same manner as in example 4 in accordance with the obtained material were as follows.
amount of tetragonal zirconia: 54 mol%
porosity: 0.1%
pore size: 0.02 μm
position of pores: mainly at triple points
carbon: not detected
bend strength: 1,280 MPa
fracture toughness: 5.0 MPa $\sqrt{m}$
Weibull modulus: 12
high temperature strength: 1,250 MPa
tristimulus values: Y=10.3, x=0.28, y=0.45 (color: light yellow)

EXAMPLE 6

VCl$_2$ having a purity of 99.5% was added to an aqueous solution so as to obtain 0.5 wt.% V$_2$O$_5$ as a colorant in the sintered material. Other conditions were the same as in example 3 and the determing procedure was the same as in example 4. The resulting data were as follows.
amount of tetragonal zirconia: 52 mol%
porosity: 0.5%
pore size: 0.04 μm
position of pores: mainly at triple points
carbon: not detected
bend strength: 1,150 MPa
fracture toughness: 5.1 MPa $\sqrt{m}$
Weibull modulus: 10
high temperature strength: 1,120 MPa
tristimulus values: Y=6.6, x=0.38, y=0.45 (color: yellow)

EXAMPLE 7

CrCl$_3$ having a purity of 99.5% was added to an aqueous solution so as to obtain 0.2 wt.% Cr$_2$O$_3$ as a colorant in the sintered material. Other conditions were the same as in example 3 and the determining procedure was the same as in example 4. The resulting data were as follows.
amount of tetragonal zirconia: 55 mol%
porosity: 0.1%
pore size: 0.02 μm
position of pores: mainly at triple points
carbon: not detected
bend strength: 1,300 MPa
fracture toughness: 5.1 MPa $\sqrt{m}$
Weibull modulus: 11
high temperature strength: 1,280 MPa
tristimulus values: Y=5.66, x=0.48, y=0.30 (color: brown)

EXAMPLE 8

CrCl$_3$ having a purity of 99.5% was added to an aqueous solution so as to obtain 0.7 wt.% Cr$_2$O$_3$ as a colorant in the sintered material. Other conditions were the same as in example 3 and the determining procedure was the same as in example 4. The resulting data were as follows.
amount of tetragonal zirconia: 52 mol% porosity: 0.3%
pore size: 0.03 μm
position of pores: mainly at triple points
carbon: not detected
bend strength: 1,250 MPa
fracture toughness: 5.0 MPa $\sqrt{m}$
Weibull modulus: 10
high temperature strength: 1,220 MPa
tristimulus values: Y=6.3, x=0.24, y=0.42 (color: green)

EXAMPLE 9

ErCl$_3$ having a purity of 99.5% was added to an aqueous solution so as to obtain 0.5 wt.% Er$_1$O$_3$ as a colorant in the sintered material. Other conditions were the same as in example 3 and the determining procedure was the same as in example 4.
amount of tetragonal zirconia: 55 mol%
porosity: 0.1%
pore size: 0.02 μm
position of pores: mainly at triple points
carbon: not detected
bend strength: 1,320 MPa
fracture toughness: 5.0 MPa $\sqrt{m}$
Weibull modulus: 11
high temperature strength: 1,300 MPa
tristimulus values: Y=12.0, x=0.42, y=0.24 (color: pink)

EXAMPLE 10

ErCl$_3$ having a purity of 99.5% was added to an aqueous solution so as to obtain 0.2 wt.% CuO as a colorant in the sintered material. Other conditions were the same as in example 3 and the determining procedure was the same as in example 4. The resulting data were as follows.
amount of tetragonal zirconia: 53 mol%
porosity: 0.1%
pore size: 0.02 μm
position of pores: mainly at triple points
carbon: not detected
bend strength: 1,280 MPa
fracture toughness: 5.5 MPa $\sqrt{m}$
Weibull modulus: 12
high temperature strength: 1,230 MPa
tristimulus values: Y=9.9, x=0.26, y=0.28 (color: blue)

EXAMPLE 11

FeCl$_2$ having a purity of 99.5% was added to an aqueous solution so as to obtain 0.5 wt.% Fe$_2$O$_3$ as a colorant in the sintered material. Other conditions were the same as in example 3 and the determining procedure was the same as in example 4. The resulting data were as follows.
amount of tetragonal zirconia: 56 mol%
porosity: 0.1%
pore size: 0.02 μm
position of pores: mainly at triple points
carbon: not detected
bend strength: 1,330 MPa
fracture toughness: 5.3 MPa $\sqrt{m}$
Weibull modulus: 13
high temperature strength: 1,310 MPa
tristimulus values: Y=7.6, x=0.47, y=0.33 (color: orange)

EXAMPLE 12

CoCl$_2$ having a purity of 99.5% was added to an aqueous solution so as to obtain 0.1 wt.%, CoO as a colorant in the sintered material. Other conditions were the same as in example 3 and the determining procedure was the same as in example 4. The resulting data were as follows.
amount of tetragonal zirconia: 53 mol%
porosity: 0.1%
pore size: 0.02 μm
position of pores: mainly at triple points
carbon: not detected
bend strength: 1,310 MPa
fracture toughness: 5.1 MPa $\sqrt{m}$
Weibull modulus: 12
high temperature strength: 1,280 MPa
tristimulus values: Y=1.30, x=0.30, y=0.20 (color: royal purple)

COMPARISON 1

The amount of yttria was set so as to bocome 1.2 mol% in the sintered material. Other conditions were the same as in example 1. The determining procedure was the same as in example 1. The resulting data were shown as follows. However, the size and position of pores could not been determined, because there were many cracks caused by the transformation from tetragonal to monoclinic and pores and the cracks could not been distinguished.
amount of tetragonal zirconia: 62 mol%
porosity: 7%
carbon: not detected
bend strength: 320 MPa
fracture toughness: 4.3 MPa $\sqrt{m}$
Weibull modulus: 5
high temperature strength: 100 MPa

COMPARISON 2

The amount of yttria was set so as to bocome 5.5 mol% in the sintered material. Other conditions were the same as in example 3. The determining procedure was the same as in example 1. The resulting data were as follows.
amount of tetragonal zirconia: 40 mol%
porosity: 0.1%
pore size: 0.02 μm
position of pores: mainly at triple points
carbon: not detected
bend strength: 600 MPa
fracture toughness: 4.5 MPa $\sqrt{m}$
Weibull modulus: 11
high temperature strength: 590 MPa

COMPARISON 3

Figure 4A:
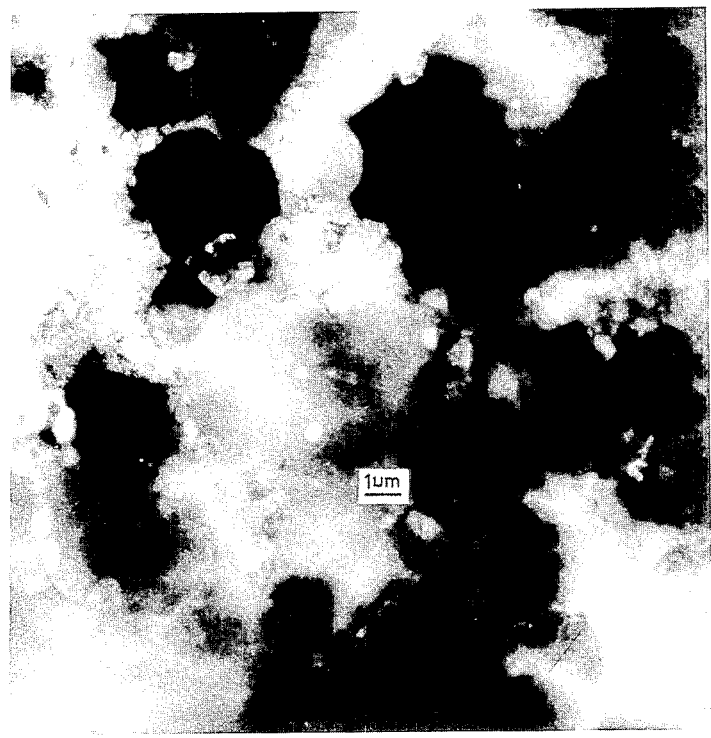
FIG. 4A is a microphotograph (magnification; 6,000) of a conventional sintered zirconia material.

The pressure when forming the green body was set to about 1,000 kg/cm$^2$. Other conditions were the same as in example 2. The determined data of the sintered material obtained were as follows.
amount of tetragonal zirconia: 90 mol%
porosity: 0.6%
pore size: 0.12 μm
position of pores: mainly at triple points
carbon: not detected
bend strength: 1,350 MPa
fracture toughness: 7.1 MPa $\sqrt{m}$
Weibull modulus: 7
high temperature strength: 1,300 MPa FIG. 4A (microphotograph, magnification: 6,000) shows the microstructure of the sintered material. FIG. 4B is a schematic view traced along FIG. 4A. In FIG. 4B, the numeral $1_d$ shows a zirconia crystal grain and the numeral $2_d$ shows pores. The pores exist in the grains, at the grain boundaries and at the triple points.

COMPARISON 4

The pressure when forming the green body was set to about 2,000 kg/cm$^2$ and the temperature for presintering was set to about 1,450° C. For HIP, a carbon heater was used and the treatment was carried out in Ar gas atmosphere at 1,400° C. Other conditions were the same as in example 2. The determining procedure was the same as in example 1. Although the existence of carbon was recognized by lazer Raman spectral analysis, the absolute amount of the carbon could not been determined by the infrared absorptiometric method. Therefore, the amount is considered to be extremely small. The resulting data were as follows.
amount of tetragonal zirconia: 94 mol%
porosity: 0.05%
pore size: 0.02 μm
position of pores: mainly at triple points
bend strength: 1,650 MPa
fracture toughness: 6.5 MPa $\sqrt{m}$
Weibull modulus: 14
high temperature strength: 500 MPa

COMPARISON 5

The temperature was set to about 1,500° C. and the pressure was set to about 2,000 kg/cm$^2$ when forming the green body, and the temperature for sintering the material was set to about 1,400° C. Other conditions were the same as in comparison 2. The determining procedure was the same as in example 1. The resulting data were as follows.
amount of tetragonal zirconia: 32 mol%
porosity: 0.1%
pore size: 0.02 μm
position of pores: mainly at triple points
carbon: not detected
bend strength: 600 MPa
fracture toughness: 5.1 MPa $\sqrt{m}$
Weibull modulus: 12
high temperature strength: 590 MPa

COMPARISON 6

A carbon heater was used for HIP after presintering and the HIP was carried out in an Ar gas atmosphere. Other conditions were the same as in example 4. The resulting data were as follows.
amount of tetragonal zirconia: 53 mol%
porosity: 0.1%
pore size: 0.02 μm
position of pores: mainly at triple points
carbon: detected by laser Raman spectral analysis
bend strength: 1,320 MPa
fracture toughness: 5.1 MPa $\sqrt{m}$
Weibull modulus: 10
high temperature strength: 400 MPa
tristimulus values: $Y=0.10$, $x=0.31$, $y=0.34$ (color: black blue)

COMPARISON 7

A carbon heater was used for HIP after presintering and the HIP was carried out in an Ar gas atmosphere. Other conditions were the same as in example 5. The resulting data were as follows.
amount of tetragonal zirconia: 54 mol%
porosity: 0.1%
pore size: 0.02 μm
position of pores: mainly at triple points
carbon: detected by laser Raman spectral analysis
bent strength: 1,270 MPa
fracture toughness: 5.5 MPa $\sqrt{m}$
Weibull modulus: 12
high temperature strength: 380 MPa
tristimulus values: $Y=0.23$, $x=0.32$, $y=0.35$ (color: black yellow)

COMPARISON 8

A carbon heater was used for HIP after presintering and the HIP was carried out in an Ar gas atmosphere. Other conditions were the same as in example 6. The resulting data were as follows.
amount of tetragonal zirconia: 52 mol%
porosity: 0.5%
pore size: 0.04 μm
position of pores: mainly at triple points
carbon: detected by laser Raman spectral analysis
bend strength: 1,160 MPa
fracture toughness: 5.1 MPa $\sqrt{m}$
Weibull modulus: 11
high temperature strength: 320 MPa
tristimulus values: $Y=0.15$, $x=0.36$, $y=0.36$ (color: black brown)

COMPARISON 9

A carbon heater was used for HIP after presintering and the HIP was carried out in an Ar gas atmosphere. Other conditions were the same as in example 8. The resulting data were as follows.
amount of tetragonal zirconia: 52 mol%
porosity: 0.3%
pore size: 0.03 μm
position of pores: mainly at triple points
carbon: detected by laser Raman spectral analysis
bend strength: 1,250 MPa
fracture toughness: 5.0 MPa $\sqrt{m}$
Weibull modulus: 11
high temperature strength: 360 MPa
tristimulus values: $Y=0.08$, $x=0.32$, $y=0.36$ (color: black green)

As shown in the above comparisons 6-9, the sintered materials obtained by using a carbon heater and in an Ar gas atmosphere for HIP were colored to black system, and a beautiful and colorful color was not obtained.

COMPARISON 10

In example 4, the material, after rubber pressing, was heated to about 900° C. at a heating rate of about 50° C./h and further heated to 1,450° C. at a heating rate of 40° C./h, and the temperature of the material was maintained at the temperature for about 2 hours, whereby a sintered material was obtained. This sintered material was determined in the same manner as in example 4. The resulting data were as follows.
amount of tetragonal zirconia: 43 mol%
porosity: 1.6%
pore size: 0.2 μm
position of pores: many pores exist in the grains and at the grain boundaries
carbon: not detected
bend strength: 500 MPa fracture toughness: 5.5 MPa $\sqrt{m}$
Weibull modulus: 10
high temperature strength: 480 MPa
tristimulus values: Y=26.5, x=0.30, y=0.37 (color: whitish light blue)

COMPARISON 11

In example 5, the material, after rubber pressing, was heated to about 900° C. at a heating rate of about 50° C./h and further heated to 1,450° C. at a heating rate of 40° C./h, and the temperature of the material was maintained for about 2 hours, whereby a sintered material was obtained. This sintered material was determined in the same manner as in example 5. The resulting data were as follows.
amount of tetragonal zirconia: 48 mol%
porosity: 1.8%
pore size: 0.2 μm
position of pores: many pores exist in the grains and at the grain boundaries
carbon: not detected
bend strength: 480 MPa
fracture toughness: 5.6 MPa $\sqrt{m}$
Weibull modulus: 11
high temperature strength: 460 MPa
tristimulus values: Y=80.1, x=0.31, y=0.38 (color: white)

COMPARISON 12

In example 6, the material, after rubber pressing, was heated to about 900° C. at a heating rate of about 50° C./h and further heated to 1,450° C. at a rate of 40° C./h, and the temperature of the material was maintained at the temperature for about 2 hours, whereby a sintered material was obtained. This sintered material was determined in the same manner as in example 6. The resulting data were as follows.
amount of tetragonal zirconia: 45 mol%
porosity: 2.0%
pore size: 0.3 μm
position of pores: many pores exist in the grains and at the grain boundaries
carbon: not detected
bend strength: 430 MPa
fracture toughness: 4.9 MPa $\sqrt{m}$
Weibull modulus: 9
high temperature strength: 400 MPa
tristimulus values: Y=50.8, x=0.35, y=0.37 (color: whitish yellow)

COMPARISON 13

In example 8, the material, after rubber pressing, was heated to about 900° C. at a heating rate of about 50° C./h and further heated to 1,450° C. at a heating rate of 40° C./h, and the temperature of the material was maintained at the temperature for about 2 hours, whereby a sintered material was obtained. This sintered material was determined in the same manner as in example 8. The resulting data were as follows.
amount of tetragonal zirconia: 49 mol%
porosity: 1.7%
pore size: 0.2 μm
position of pores: many pores exist in the grains and at the grain boundaries
carbon: not detected
bend strength: 480 MPa
fracture toughness: 5.2 MPa $\sqrt{m}$
Weibull modulus: 11
high temperature strength: 450 MPa
tristimulus values: Y=71.6, x=0.30, y=0.39 (color: whitish green)

COMPARISON 14

CrCl$_3$ having a purity of 99.5% was added to an aqueous solution so as to obtain 3.0 wt.% Cr$_2$O$_3$ as a colorant in the sintered material. The manufacturing conditions of forming the green body were the same as in example 3. The material was heated to about 900° C. at a heating rate of about 50° C./h and further heated to 1,450° C. at a heating rate of 40° C./h, and the temperature of the material was maintained for about 2 hours, whereby a sintered material was obtained. This sintered material was determined in the same manner as in example 8. The resulting data were as follows.
amount of tetragonal zirconia: 48 mol%
porosity: 1.9%
pore size: 0.2 μm
position of pores: many pores exist in the grains and at the grain boundaries
carbon: not detected
bend strength: 410 MPa
fracture toughness: 5.0 MPa $\sqrt{m}$
Weibull modulus: 10
high temperature strength: 360 MPa
tristimulus values: Y=9.9, x=0.28, y=0.42 (color: slightly dark green)

As shown in the above comparison 10–14, compared with the material obtained in example 4–8, each sintered material obtained by adding a colorant and sintering under an ambient pressure did not have a transparent feeling. The color of the material did not have depth because the color became whitish, and the color became light, even if the same amount of colorant as in example 4–8 was added. One of the reasons is that the porosity and the pore size is very large. In the present invention, by suppressing the porosity to not greater than 0.6% and suppressing the pore size to not greater than 0.1 μm, the sintered material can have a dark and deep color.

As described in detail in the above, since the sintered zirconia material according to the present invention contains at least 50 mol% tetragonal zirconia and 1.5–5 mol% yttria, the porosity is not greater than 0.6%, the pore size is not greater than 0.1 μm and the pores exist mainly at triple points, the strength and toughness of the material can be increased and the deviation thereof is very small. Since the material substantially does not contain carbon, the decrease of the strength can be almost prevented, even if it is used under the condition of higher than 600° C.

Moreover, the sintered zirconia material according to the present invention can have the characteristic of light transmission and also can have a deep color.

Therefore, the sintered material can be applied to various uses. The uses are shown hereunder.

A. a material for a part of a internal combusion engine such as a sub-combustion chamber, a turbocharger, a piston cap, a cylinder, a cylinder liner, a plate exhaust valve head, a blade of a gas turbine, a combustor, a nose cone, a shroud, a heat insulator, and an exhaust valve for a diesel engine (a valve, a valve body and a valve box);

B. a material for a part of various industrial machines such as a die, a nozzle, a capillary, a block or a gauge for detailed survey, a ring, a heating cylinder, an insulating spacer, an insulating sleeve, a mechanical seal, a plunger pump, a punch, a spring, a coil spring, a tool for contraction, a bearing, a ball for a bearing, a ball for a mill, a guide roll, a roll for a rolling mill, an impeller of a pump for a slurry, a screw, a sleeve, a valve, an orifice, a tile, a sleeve for wire wrapping, a driver, a thread guide;

C. a material for cutlery such as a cutter (a slitter, a circular shear) or a high temperature knife for a fiber, a paper, a film or a magnetic tape, a razor blade, a blade of a hair clipper, scissors, a knife and a kitchen knife;

D. a material for a medical tool or a medical material such as a surgical knife, tweezers, a root of a tooth, a tooth crown, an arthrosis and a fixing material for a bone;

E. a material for an ornament or substitute for jewelry such as an imitation of jewel, a seal impression, tie pin, cuff links and a part of a watch;

F. a material for a sport or leisure tool such as a go stone, a golf club and a fishing line guide;

G. a material for a tableware such as a spoon, a fork and a dish;

H. a material for a tool for writing such as a ball for a ball-point pen and a tip portion of a pen.

Although only several preferred embodiments of the present invention have been described in detail, it will be appreciated by those skilled in the art that various modifications and alterations can be made to the particular embodiments shown without materially departing from the novel teachings and advantages of this invention.

Accordingly, it is to be understood that all such modifications and alterations are included within the scope of the invention as defined by the following claims.

What is claimed is:

1. A sintered zirconia material which comprises: a substantially carbon free sintered material which contains at least 50 mol% zirconia having a tetragonal crystal structure; wherein said sintered material contains from 1.5 to 5 mol% yttria; wherein the porosity of said sintered material is not greater than 0.6%; wherein the pore size of said sintered material is not greater than 0.1 $\mu$m; and wherein the pores of said sintered material exist mainly at triple points of the zirconia grain boundaries.

2. The sintered material of claim 1, wherein the sintered material contains not less than 70 mol% zirconia having a tetragonal crystal structure.

3. The sintered material of claim 2, wherein the sintered material contains not less than 80 mol% zirconia having a tetragonal crystal structure.

4. The sintered material of claim 1, wherein the amount of zirconia having a monoclinic crystal structure present in the sintered material is not greater than 10 mol%.

5. The sintered material of claim 1, wherein the sintered material additionally contains zirconia having a cubic crystal structure.

6. The sintered material of claim 1, wherein the sintered material contains 1.75 to 4.5 mol% yttria.

7. The sintered material of claim 1, wherein the porosity of the sintered material is not greater than 0.4%.

8. The sintered material of claim 7, wherein the porosity of the sintered material is not greater than 0.3%.

9. The sintered material of claim 1, wherein the pore size is not greater than 0.05 $\mu$m.

10. The sintered material of claim 1, wherein not less than 80% of the pores existing at triple points of the sintered material have a pore size of not greater than 0.1 $\mu$m.

11. The sintered material of claim 10, wherein not less than 90% of the pores existing at triple points of the sintered material have a pore size of not greater than 0.1 $\mu$m.

12. The sintered material of claim 1, wherein not less than 80% of the pores of the sintered material exist at the triple points of the zirconia grain boundaries.

13. The sintered material of claim 12, wherein not less than 90% of the pores of the sintered material exist at the triple points of the zirconia grain boundaries.

14. The sintered material of claim 1, wherein the sintered material additional contains at least one metal oxide selected from the group consisting of aluminum, titanium, copper, nickel, iron, cobalt and chromium in an amount of from 0.1 to 1 wt.% as a third component.

15. The sintered material of claim 14, wherein the third component is present in an amount of from 0.2 to 0.5 wt.%.

16. The sintered material of claim 1, wherein the sintered material additionally contains at least one colorant selected from the group consisting of 0.05 to 0.7 wt.% chromium oxide, 0.05 to 0.2 wt.% copper oxide, 0.05 to 2 wt.% erbium oxide, 1 to 2 wt.% cerium oxide, 0.05 to 2 wt.% vanadium oxide, 0.5 to 2 wt.% neodymium oxide, 0.05 to 0.3 wt.% cobalt oxide, and 0.05 to 0.5 wt.% iron oxide.

17. A method for manufacturing a sintered zirconia material comprising the steps of:
   (a) preparing a zirconia powder which contains from 1.5 to 5 mol% yttria powder;
   (b) making a raw material formed as a solid solution with said yttria and said zirconia powders by milling said powders after calcining said powders at 800° to 1,000° C.;
   (c) forming a green body by compacting said raw material;
   (d) making a presintered material which has a bulk density that is not less than 95% of a theoretical density by presintering said green body; and
   (e) sintering said presintered material in an oxidizing atmosphere by hot isostatic pressing.

18. A method for manufacturing a sintered zirconia material comprising the steps of:
   (a) preparing a zirconia powder which contains from 1.5 to 5 mol% yttria powder;
   (b) making a raw material formed as a solid solution with said yttria and said zirconia powders by milling said powders after calcining said powders at 800° to 1,000° C.;
   (c) forming a green body by compacting said raw material; and
   (d) putting said green body into a capsule, presintering and then sintering said green body in an oxidizing atmosphere by hot isostatic pressing.

19. A method for manufacturing a sintered zirconia material comprising the steps of:
   (a) preparing a zirconia powder which contains from 1.5 to 5 mol% yttria powder;
   (b) making a raw material formed as a solid solution with said yttria and said zirconia powders by milling said powders after calcining said powders at 800° to 1,000° C.;
   (c) filling said raw material in a capsule, presintering and then sintering said raw material by directly consolidating said raw material in an oxidizing atmosphere using hot isostatic pressing.

20. The manufacturing method of claim 17, 18, or 19, wherein the zirconia and yttria powders are prepared from an aqueous solution containing zirconium chloride having a plurity of not less than 99.9% and an aqueous solution containing yttrium chloride having a purity of not less than 99.5%.

21. The manufacturing method of claim 17, 18, or 19, wherein the zirconia and yttria powders are prepared from an aqueous solution containing zirconium nitrate having a purity of not less than 99.9% and an aqueous solution containing yttrium nitrate having a purity of not less than 99.5%.

22. The manufacturing method of claim 17, 18, or 19, wherein the zirconia and yttria powders are prepared from a zirconia powder having a purity of not less than 99.9% and a yttria powder having a purity of not less than 99.9%.

23. The manufacturing method of claim 17, 18 or 19, wherein the temperature of the calcination is 850° to 950° C.

24. The manufacturing method of claim 17, 18, or 19, wherein the raw material additionally contains at least one metal oxide selected from the group consisting of aluminum, titanium, copper, nickel, iron, cobalt and chromium oxide in an amount of 0.1–1 wt.% as a third component.

25. The manufacturing method of claim 24, wherein the third component is present in an amount of 0.2–0.5 wt.%.

26. The manufacturing method of claim 17, 18, or 19, wherein the raw material additionally contains at least one colorant selected from the group consisting of 0.05 to 0.7 wt.% chromium oxide, 0.05 to 0.2 wt.% copper oxide, 0.05 to 2 wt.% erbium oxide, 1 to 2 wt.% cerium oxide, 0.05 to 2 wt.% vanadium oxide, 0.5 to 2 wt.% neodymium oxide, 0.05 to 0.3 wt.% cobalt oxide, and 0.05 to 0.5 wt.% iron oxide.

27. The manufacturing method of claim 17, 18 or 19, wherein the oxygen concentration of the oxidizing atmosphere is 0.1 to 25 vol.%.

28. The manufacturing method of claim 27, wherein the oxygen concentration is 1 to 20 vol.%.

29. The manufacturing method of claim 28, wherein the oxygen concentration is 3 to 10 vol.%.

30. The manufacturing method of claim 17, 18 or 19, wherein the gas pressure of the oxidizing atomsphere is 1,000 to 2,200 kg/cm$^2$.

31. The manufacturing method of claim 30, wherein the gas pressure is 1,500 to 2,000 kg/cm$^2$.

32. The manufacturing method of claim 17, wherein the bulk density of the presintered material is not less than 97.5% of the theoretical density.

33. The manufacturing method of claim 32, wherein the bulk density of the presintered material is not less than 99% of the theoretical density.

34. The manufacturing method of claim 17, wherein the presintered material is made by first heating the green body to from 850° to 1,000° C. at a heating rate of about 20° to 100° C./hour and then secondly heating said green body to from 1,150° to 1,550° C. at a heating rate of about 30° to 50° C./hour and maintaining said green body at the temperature after the second heating.

35. The manufacturing of claim 34, wherein the heating rate of the first heating is 30° to 70° C./hour.

36. The manufacturing method of claim 35, wherein the heating rate of the first heating is 30° to 50° C./hour.

37. The manufacturing method of claim 34, wherein the temperature of the body after the first heating is 900° to 950° C.

38. The manufacturing method of claim 34, wherein the temperature of the body after the second heating is 1,200° to 1,450° C.

39. The manufacturing method of claim 17, wherein the presintered material is sintered by heating said material to from 1,150° to 1,500° C., maintaining said material at this temperature and cooling said material to room temperature at a cooling rate of about 200° to 600° C./hour.

40. The manufacturing method of claim 39, wherein the temperature for sintering is 1,300° to 1,400° C.

41. The manufacturing method of claim 39, wherein the cooling rate is 300° to 500° C./hour.

* * * * *